(12) United States Patent
Dautel et al.

(10) Patent No.: US 9,109,119 B2
(45) Date of Patent: Aug. 18, 2015

(54) CHROMOPHORES, METHOD FOR THE PREPARATION THEREOF, AND USE OF SAME

(75) Inventors: Olivier Dautel, Montpellier (FR); Joel Moreau, Montpellier (FR); Jean-Pierre Lere-Porte, Montpellier (FR)

(73) Assignee: CENTRE NATIONAL DE LA RECHERCHE SCIENTIFIQUE-CNRS, Paris (FR)

( * ) Notice: Subject to any disclaimer, the term of this patent is extended or adjusted under 35 U.S.C. 154(b) by 1100 days.

(21) Appl. No.: 13/063,897

(22) PCT Filed: Sep. 15, 2009

(86) PCT No.: PCT/FR2009/051735
§ 371 (c)(1),
(2), (4) Date: Mar. 14, 2011

(87) PCT Pub. No.: WO2010/029274
PCT Pub. Date: Mar. 18, 2010

(65) Prior Publication Data
US 2011/0172439 A1    Jul. 14, 2011

(30) Foreign Application Priority Data
Sep. 15, 2008    (FR) ...................... 08 56179

(51) Int. Cl.
| C07D 403/10 | (2006.01) |
| C07D 403/14 | (2006.01) |
| C08G 77/04 | (2006.01) |
| C09B 23/01 | (2006.01) |
| C09B 69/00 | (2006.01) |

(52) U.S. Cl.
CPC .......... *C09B 23/0075* (2013.01); *C07D 403/10* (2013.01); *C07D 403/14* (2013.01); *C08G 77/04* (2013.01); *C09B 23/0066* (2013.01); *C09B 69/008* (2013.01)

(58) Field of Classification Search
None
See application file for complete search history.

(56) References Cited

U.S. PATENT DOCUMENTS 8,722,318 B2 * 5/2014 Dautel et al. .................. 430/322

FOREIGN PATENT DOCUMENTS

WO    WO-2007/120788 A1    10/2007

OTHER PUBLICATIONS

Sallenave, et al., Adv. Func. Mat., 19:404 (2009, published Dec. 18, 2008).*
Dautel, et al. "Confined photactive substructures on a chiral scaffold: the design of an electroluminescent polyimide as material for PLED," J. Mater. Chem. 15:4446-4452 (2005).
Dautel, et al., "Nanostructuration of Phenylenevinylenediimide-Bridged Silsesguioxane: From Electroluminescent Molecular J-Aggregates to Photoresponsive Polymeric H-Aggregates," J. Am. Chem. Soc. 128:4892-4901 (2006).
Grigg, et al. "Intermolecular Heck-Diels-Alder Cascade Processes of Alkylallenes," Tetrahedron Letters 39:3247-3250 (1998).
International Search Report from PCT/FR2009/0517 dated May 25, 2010.
Wantz, et al., "Layered organic film growth by substrate temperature tuning for efficiency-enhanced OLEDs," Organic Electronics 7:38-44 (2006).
Wantz, et al., "Temperature-dependent electroluminescence spectra of organic light emitting diodes based on thermally evaporated bis-imido-phenylene vinylene derivative," Applied Physics Letters: 90:162104-1 to 162104-3 (2007).

* cited by examiner

*Primary Examiner* — Michael Barker
(74) *Attorney, Agent, or Firm* — McAndrews, Held & Malloy Ltd.

(57) ABSTRACT

The invention relates to a chromophore of general formula:

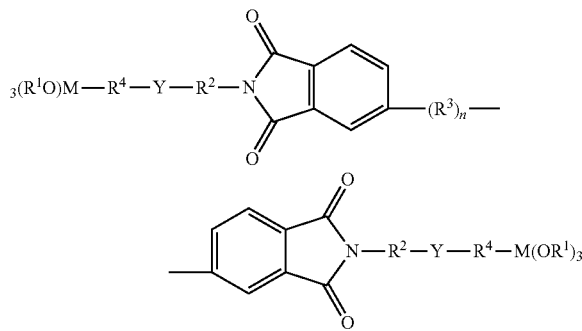

in which:
$R^1$ represents $C_1$-$C_4$ alkyl;
$R^2$ represents a sterically hindered group;
$R^3$ represents a pi-conjugated system;
Y represents O, S, NH or is absent;
$R^4$ represents a $C_3$-$C_{18}$, preferably $C_3$-$C_8$ and more preferably $C_3$ alkyl group;
M represents a metal from Group III or IV of the Periodic Table;
n is an integer,
to its process of preparation and to its uses.

20 Claims, 1 Drawing Sheet

Fig.1a

Fig.1b

CHROMOPHORES, METHOD FOR THE PREPARATION THEREOF, AND USE OF SAME

The present invention relates to novel chromophores, to their process of synthesis and to their use.

In the present patent application, the term "chromophore" is understood to mean a molecule of pi type. A molecule of pi type is composed of an atom or group of atoms through which electrons can be delocalized. Preferably, the orbitals which make possible this delocalization of the electrons are the p orbitals of carbon atoms having multiple bonds, such as, for example, those of alkenes, alkynes, neutral or charged aromatic nuclei, or cyclic systems comprising heteroatoms.

The chromophore has an ability to absorb the energy of the photons in the visible spectral region; consequently, the delocalized electrons can come into resonance with the incident radiation. These molecules will thus change in color in response to the photoexcitation.

The chromophore shows optoelectronic properties; consequently, it is used in the manufacture of electronic components which emit or interact with light; it makes it possible to convey, memorize and amplify optical signals by purely optical means.

Recently, the present inventors have reported a novel class of compounds which are highly fluorescent and electroluminescent in solution and in the solid state using a cyclohexyl fragment as structural agent directing the aggregation of the chromophore towards a J-type aggregation [1]. The imide functional group introduced makes it possible in particular to tune the electronic properties towards a better balance between the mobility of the holes and the mobility of the electrons but also allows easy functionalization of the chromophore. In the same way, by using the triethoxysilane functional group as structuring agent, the present inventors had been able to synthesize a highly fluorescent and electroluminescent hybrid precursor [2]. The material resulting from the conventional hydrolysis/polycondensation of the precursor shows a modification of the supramolecular organization of the chromophore from a J-type aggregation to an H-type aggregation. The hybrid films thus produced no longer exhibit fluorescence properties but high photoconductivities.

It was therefore necessary to make available to a person skilled in the art chromophore compounds which exhibit high conductivity properties while being strongly fluorescent.

The present inventors have found that the compounds of the invention exhibit both these properties.

The invention thus relates to chromophore compounds of formula (I) below:

in which:
$R^1$ represents $C_1$-$C_4$ alkyl;
$R^2$ represents a sterically hindered group;
$R^3$ represents a pi-conjugated system;
Y represents O, S, NH or is absent;
$R^4$ represents a $C_3$-$C_{18}$, preferably $C_3$-$C_8$ and more preferably still $C_3$ alkyl group;
M represents a metal from Group III or IV of the Periodic Table;
n is an integer.

The chromophore compound is either a polymer or an oligomer, depending on the value of the integer n. The integer n can be comprised between 1 and 10,000, preferably between 1 and 100 and more preferably still between 1 and 20. However, it is easier to operate with oligomers or small polymers for which n is comprised between 1 and 19, preferably between 1 and 15, and more preferably still between 1 and 10.

The term "$C_1$-$C_4$ alkyl" is understood to mean methyl, ethyl, n-propyl, isopropyl, n-butyl, isobutyl, tert-butyl.

Mention may be made, as metal M, of Si, Ti, Zr, Sn, Al. Preferably, M is Si.

Mention may be made, as example of sterically hindered group $R^2$, of the groups chosen from the group comprising:

Mention may be made, as example of pi-conjugated system $R^3$, of those chosen from the group comprising:

with R representing H or a $C_1$-$C_{18}$, preferably $C_1$-$C_{12}$ and more preferably still $C_1$-$C_8$ alkyl group, said alkyl group optionally being branched or substituted by a heteroatom (O, S, N and the like).

This novel chromophore, the precursor of highly fluorescent hybrid materials, exhibits excellent optoelectronic properties. The crosslinkable $M(OR^1)_3$ group makes it possible to employ the sol-gel process. The sterically hindered group prevents aggregation after hydrolysis polycondensation, which makes it possible to retain the emission properties in the hybrid material.

This novel chromophore is prepared by a process which comprises a step consisting of the introduction of the bulky group $R^2$ by condensation of an aliphatic or aromatic amine comprising this group with 4-bromophthalic anhydride. This stage of the process will be described in more detail below.

The chromophore preparation process in accordance with the invention comprises a step of hydrometallation of a hydrogenotrialkoxymetal [$HM(OR^1)_3$], catalyzed by Karstedt catalyst. The hydrometallation is carried out on the condensation product with 4-bromophthalic anhydride and the aromatic or aliphatic amine.

The process additionally comprises a subsequent step of organometallic coupling between the trialkoxymetallated intermediate and a pi-conjugated system comprising $R^3$.

The method of introduction of the bulky group $R^2$ will depend on its nature.

In the case of an aliphatic bulky group $R^2$, the introduction thereof is carried out according to the following general process:

in which $R^2$ and Y are as defined above.

According to a preferred embodiment, $HYR^2$—$NH_2$ is an aminoalcohol derivative of the bulky group, of the HO—$R^2$—$NH_2$ type.

Examples of aminoalcohols which can be used are:

The hydrometallation reaction is carried out on the compound 2, modified by insertion of an $R^{i4}$ group ($R^{i4}$ representing an alkyl group exhibiting the same carbon number as the $R^4$ group and exhibiting an ethylenic unsaturation), according to the following general process:

$R^1$, $R^2$, $R^3$, $R^4$ and Y being as defined above.

In particular, the process is then carried out according to the following reaction scheme:

The aminoalcohol is first of all condensed with the anhydride 1 at reflux in toluene in a Dean-Stark assembly in order to obtain the imidoalcohol 2a. The alkylation of the alcohol by the allyl bromide in the presence of a base provides 3a with good yields. The hydrosilylation of the vinyl functional group by $HM(OR^1)_3$ catalyzed by the Karstedt catalyst provides the intermediate 4a.

In the case of an aromatic bulky group $R^2$, its introduction is carried out according to the following reaction scheme:

Mention may be made, as example of $R^2$—$NH_2$, of the following benzamines:

The hydrometallation reaction is carried out on compound 7 according to the following general process:

According to a preferred embodiment, this process employs a benzamine derived from the bulky group of $R^2$—$NH_2$ type, according to the following reaction scheme:

In a first step, the allylation of the amine functional group is carried out by heating an equimolar mixture of benzamine and allyl bromide at 120° C. for two days.

The key step relates to the rearrangement of the N-allyl-benzamine 5a to give para-allylbenzamine 10a. It is carried out by the action of the zinc chloride at reflux of xylene with excellent yield (≈80%).

The hydrosilylation of the vinyl functional group by $HM(OR^1)_3$ catalyzed by the Karstedt catalyst provides the intermediate 8a.

Finally, two trialkoxymetallated intermediates, either of formula 4 (or 4a) or else of formula (8 or 8a) are used in an organometallic coupling with the pi-conjugated system.

According to a preferred form of the invention, the chromophore exhibits the formula:

with $M=S^1$, $R^1$=ethyl, $R^2$=cyclohexyl, n=1, $R^3$=1,4-bis(octyloxy)-2,5-divinylbenzene, $R^4$=—$CH_2CH_2CH_2$— and Y=O.

This compound is prepared according to the following reaction scheme:

-continued

In a first step, trans-aminocyclohexanol and the anhydride 1[3] are condensed by heating at reflux in toluene in a Dean-Stark assembly in order to provide 2b after recrystallization of the crude product. The alkylation of the alcohol by allyl bromide in the presence of a base gave 3b with a good yield. The hydrosilylation of the vinyl functional group by HSi(OEt)$_3$ catalyzed by the Karstedt catalyst provides the intermediate 4b, isolated by chromatography on silica gel. 4b is coupled to 1,4-divinyl-2,5-bis(octyloxy)benzene 9 in the presence of a palladium catalyst. The Heck reaction is carried out in dry N,N-dimethylformamide in the presence of Pd(OAc)$_2$ and P(o-C$_6$H$_4$Me)$_3$. Finally, the conjugated precursor 6 was isolated by recrystallization in ethanol to provide a yellow powder with a yield of 24%. This novel silylated precursor is soluble in the majority of organic solvents, highly fluorescent and emits in the green under an irradiation at 430 nm in tetrahydrofuran (THF) [THF, $v_{abs\_max}$=432 nm; $v_{em\_max}$=530 nm ($v_{ex}$=430 nm)].

The chromophore according to the invention can be used in a sol-gel process for the formation of a thin film. It constitutes an excellent precursor of a thin film which is both fluorescent and exhibits excellent photoconductivity properties.

Thus, the invention also relates to the use of a chromophore as defined above or as prepared above as thin film precursor in a sol-gel process.

Very particularly, the invention relates to a method for the stabilization of the J-type aggregation in a thin film obtained by sol-gel process, characterized in that the precursor chromophore of the thin film comprises a sterically hindered group covalently bonded to the crosslinkable group. Advantageously, in this method the sterically hindered group is chosen from the group comprising:

and the crosslinkable group is a silylated group. Preferably, the sterically hindered group is the cyclohexyl and the crosslinkable group is the trimethoxysilyl or the triethoxysilyl.

The present invention will be described in more detail using the following examples, which are given purely by way of illustration and which cannot limit the scope thereof.

EXAMPLES

Example 1

4-Aminocyclohexanol (1.04 g, 8.81 mmol) and 1 ml of triethylamine were added to a solution of 5-bromoisobenzofuran-1,3-dione 1 (2 g, 8.81 mmol) in 150 ml of toluene and 50 ml of DMF. After refluxing overnight at 140° C. in a Dean-Stark assembly, the solvent was evaporated and the residue was purified by recrystallization in ethanol. 1.7 g of compound of formula 2b were obtained in the form of a white solid (yield: 58%).

M.p.: 196-197° C.

$^1$H NMR (CDCl$_3$) δ ppm: 7.94 (d, J=1.2 Hz, 1H); 7.83 (dd, J=8, 1.6 Hz, 1H); 7.67 (d, J=8 Hz, 1H); 4.11 (tt, J=12.4, 4 Hz, 1H); 3.75 (tt, J=11.2, 4.4 Hz, 1H); 2.31 (m, 2H); 2.09 (m, 2H); 1.74 (m, 2H); 1.43 (m, 2H).

$^{13}$C NMR (CDCl$_3$) δ ppm: 167.5; 166.9; 136.8; 133.6; 130.4; 128.8; 126.5; 124.5; 69.5; 49.9; 34.7; 27.4.

IR max/cm$^1$: 3326; 2935; 2862; 1769; 1709; 1606; 1459; 3417; 1374; 1170; 1152; 1092; 1063; 901; 740.

HR MS (FAB$^+$; NBA): m/z 324.0243 (M+H); calc. for C$_{14}$H$_{15}$BrNO$_3$: 324.0235.

A crown ether (30 mg, 11.7 mmol), potassium-tert-butylate (1.3 g, 11.7 mmol) and then, at 0° C., fractionwise, allyl bromide (7 g, 57.8 mmol) were added under a nitrogen atmosphere to a solution of the compound of formula 2b above (3.8 g, 11.7 mmol) in 50 ml of anhydrous THF. After stirring at ambient temperature for 2 hours, the solution was hydrolyzed with 40 ml of water. The THF was removed and the residue was extracted with dichloromethane (3×50 ml). The organic layer was dried over Na$_2$SO$_4$ and concentrated. The product was purified by column chromatography (silica, dichloromethane) to give 2.35 g of 2-(4-allyloxycyclohexyl)-5-bromoisoindoline-1,3-dione of formula 3b in the form of a white solid (yield: 55%).

M.p.: 133-134° C.

$^1$H NMR (CDCl$_3$) δ ppm: 7.94 (d, J=1.6 Hz, 1H); 7.83 (dd, J=7.8, 2 Hz, 1H); 7.64 (d, J=8 Hz, 1H); 5.93 (m, 1H); 5.28 (d, J=17.2 Hz, 1H); 5.17 (d, J=10.4 Hz, 1H); 4.12 (tt, J=12.4, 4 Hz, 1H); 4.03 (d, J=5.6 Hz, 2H); 3.40 (tt, J=11.2, 4.4 Hz, 1H); 2.27 (m, 2H); 2.16 (m, 2H); 1.76 (m, 2H) 1.38 (m, 2H).

$^{13}$C NMR (CDCl$_3$) δ ppm: 167.6; 167.1; 137.0; 135.4; 133.7; 130.6; 128.9; 126.6; 124.6; 116.9; 76.2; 69.5; 50.3; 31.6; 27.7.

IR max/cm$^1$: 2945; 2862; 1772; 1702; 1606; 1456; 1417; 1374; 1170; 1137; 1100; 1087; 1071; 920; 741.

HR MS (FAB$^+$; NBA): m/z=364.0539 (M+H); calc. for C$_{17}$H$_{19}$BrNO$_3$: 364.0548.

Triethoxysilane (1 g, 6.08 mmol) and, dropwise, Karstedt catalyst (0.17 ml, 0.4%) were added, at 0° C. and under a nitrogen atmosphere, to a solution of the compound of formula 3b (2 g, 5.5 mmol) in 10 ml of anhydrous THF. After 1 h at ambient temperature, the THF was removed and the residue was purified by flash chromatography (silica, dichloromethane and then dichloromethane/diethyl ether 2/1). 2.09 g of 5-bromo-2-(4-(3-(triethoxysilyl)-propyloxy)cyclohexyl)isoindoline-1,3-dione of formula 4b were obtained, in the form of a white solid (yield: 72%).

M.p.: 106° C.

$^1$H NMR (CDCl$_3$) δ ppm: 7.94 (d, J=1.6 Hz, 1H); 7.83 (dd, J=8.2 and 1.6 Hz, 1H); 7.67 (d, J=8 Hz, 1H); 4.11 (tt, J=12 and 4 Hz, 1H); 3.83 (q, J=6.8 Hz, 6H); 3.44 (d, J=6.8 Hz, 2H); 3.33 (tt, J=10.8 and 4 Hz, 1H); 2.27 (m, 2H); 2.15 (m, 2H); 1.75 (m, 2H); 1.68 (m, 2H); 1.35 (m, 2H); 1.22 (t, J=6.8 Hz, 9H); 0.64 (t, J=8.4 Hz, 2H).

$^{13}$C NMR (CDCl$_3$) δ ppm: 167.6; 167.1; 137.0; 133.7; 130.6; 128.8; 126.6; 124.6; 76.7; 70.8; 58.5; 50.4; 31.7; 27.7; 23.5; 18.4; 6.6.

IR max/cm$^{-1}$: 2972; 2939; 2870; 1772; 1712; 1606; 1418; 1372; 1169; 1103; 1084; 958; 904; 742.

HR MS (FAB$^+$; NBA): m/z=528.1368 (M+H); calc. for C$_{23}$H$_{35}$BrNO$_6$Si: 528.1359.

A mixture of the product of formula 4b above (825 mg, 1.56 mmol), of 1,4-bis(octyloxy)-2,5-divinylbenzene (compound 9) (300 mg, 0.78 mmol), of palladium acetate (14.1 mg, 0.066 mmol) and of tri(o-tolyl)phosphine (76.8 mg, 0.26 mmol) in 5 ml of anhydrous THF was heated, under a nitrogen atmosphere, to 100° C. and then triethylamine (0.5 g, 0.17 ml, 5 mmol) was added. After 6 h at 100° C. and cooling, the solvent was removed and the residue was purified by recrystallization in ethanol after a hot filtration intended to remove insoluble material. 260 mg of compound of formula 6 were obtained in the form of a yellow solid (yield: 24%).

M.p.: 181-182° C.

$^1$H NMR (CDCl$_3$) δ ppm: 7.97 (s, 2H); 7.77 (m, 4H); 7.63 (d, J=16.5 Hz, 2H); 7.26 (d, J=16 Hz, 2H); 7.12 (s, 2H); 4.14 (tt, J=12.4 and 4 Hz, 2H); 4.08 (t, J=6.8 Hz, 4H); 3.83 (q, J=7.2 Hz, 12H); 3.46 (t, J=7.2 Hz, 4H); 3.56 (tt, J=11.2 and 4 Hz, 2H); 2.31 (m, 4H); 2.16 (m, 4H); 1.90 (qu, J=7.2 Hz, 4H); 1.78 (m, 4H); 1.70 (m, 4H); 1.54 (qu, J=8 Hz, 4H); 1.45-1.25 (m, 20H); 1.23 (t, J=7.2 Hz, 18H) 0.87 (t, J=6.8 Hz, 6H); 0.65 (t, J=8.4 Hz, 4H).

$^{13}$C NMR (CDCl$_3$) δ ppm: 168.4; 168.2; 151.4; 151.4; 144.1; 132.9; 131.8; 130.1; 127.6; 127.5; 126.7; 123.5; 120.4; 110.9; 70.7; 69.5; 58.4; 50.1; 31.8; 31.7; 29.4; 29.3; 27.7; 26.3; 23.5; 22.7; 18.3; 14.1; 6.6.

IR max/cm$^1$: 2974; 2931; 2860; 1767; 1703; 1611; 1436; 1375; 1203; 1167; 1106; 1082; 961; 747.

Elemental analysis calc. for C$_{72}$H$_{108}$N$_2$O$_{14}$Si$_2$: C, 67.47; H, 8.49; N, 2.19. found: C, 66.57; H, 8.26; N, 2.11.

Example 2

A 30 mg/ml solution of 5,5'-(1E,1'E)-2,2'-(2,5-bis(octyloxy)-1,4-phenylene)bis(ethene-2,1-diyl)bis(2-(4-(3-(triethoxysilyl)propoxy)cyclohexyl)isoindoline-1,3-dione) (compound 6) in THF was prepared. Starting from this solution, a thin film with a thickness of 100 nm was prepared by spin coating on a silicon wafer.

A topographic study of layers spin coated onto silicon wafers was carried out by atomic force microscopy (AFM) in tapping mode using a Dimension 3100 Veeco Instruments device. The image of the topography of the wafer of the compound 6 is given in FIG. 1a and the topographic profile is given in FIG. 1b. The topographic profile of a film with a thickness of 100 nm starting from the precursor not having the cyclohexyl group[2] is also given in FIG. 1b by way of comparison.

Figure 1A:
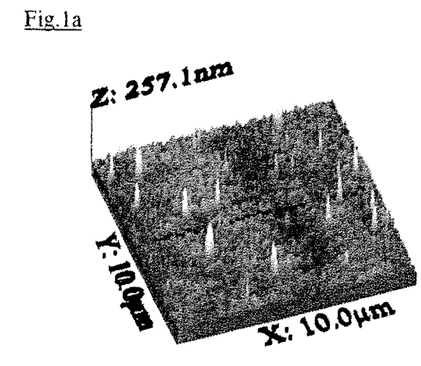
Figure 1B:
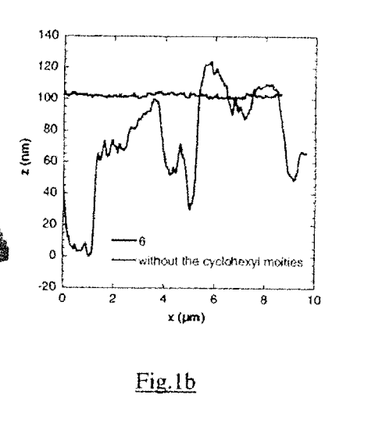

The roughness of the film obtained with the compound 6 as precursor is 1 nm. The comparative film is, for its part, extremely heterogeneous; its roughness is 40 nm.

[1] G. Wantz, O. J. Dautel, R., Almairac, L. Hirsh, F. Serein-Spirar, L. Vignau, J.-P. Lere-Porte, J. P. Parneix and J. J. E. Moreau, *Org. Elec.*, 2006, 7, 38.

[2] O. J. Dautel, G. Wantz, R. Almairac, D. Flot, L. Hirsh, J.-P. Lere-Porte, J. P. Parneix, F. Serein-Spirau, L. Vignau and J. J. E. Moreau, *J. Am. Chem. Soc.*, 2006, 128, 4892.

[3] O. J. Dautel, G. Wantz, D. Flot, Lere-Porte, J. J. E. Moreau, J. P. Parneix, F. Serein-Spirau and L. Vignau, *J. Mat. Chem.*, 2005, 41, 4446.

What is claimed is:

1. A process for the preparation of a chromophore of general formula:

in which:
R¹ represents $C_1$-$C_4$ alkyl;
R² represents a sterically hindered group;
R³ represents a pi-conjugated system;
Y represents O, S, NH or is absent;
R⁴ represents a $C_3$-$C_{18}$ alkyl group;
M represents a metal from Group III including Group III-A and Group III-B or from Group IV including Group IV-A and Group IV-B of the Periodic Table;
n is an integer,
wherein the sterically hindered group is chosen from the group consisting of:

and
wherein R³ is chosen from the group consisting of:

with R representing H or a $C_1$-$C_{18}$, alkyl group, said alkyl group optionally being branched or substituted by a heteroatom chosen in the group consisting of O, S and N, wherein said process comprises a step consisting of the introduction of the group R² by condensation of an aliphatic or aromatic amine comprising the R² group with 4-bromophthalic anhydride.

2. The process according to claim 1, which is carried out according to one of the following reaction schemes:

-continued

$R^2$ and Y being as defined in claim 1 and $R^4$ representing an alkyl group exhibiting the same carbon number as the $R^4$ group and exhibiting an ethylenic unsaturation.

3. A process for the preparation of a chromophore of general formula:

in which:
   $R^1$ represents $C_1$-$C_4$ alkyl;
   $R^2$ represents a sterically hindered group;
   $R^3$ represents a pi-conjugated system;
   Y represents O, S, NH or is absent;
   $R^4$ represents a $C_3$-$C_{18}$ alkyl group;
   M represents a metal from Group III including Group III-A and Group III-B or from Group IV including Group IV-A and Group IV-B of the Periodic Table;
   n is an integer,
wherein the sterically hindered group is chosen from the group consisting of:

and
wherein $R^3$ is chosen from the group consisting of:

with R representing H or a $C_1$-$C_{18}$ alkyl group, said alkyl group optionally being branched or substituted by a heteroatom chosen in the group consisting of O, S and N, wherein said process comprises a step of hydrometallation of a hydrogenotrialkoxymetal catalyzed by Karstedt catalyst.

4. The preparation process according to claim 3, which is carried out according to one of the following reaction schemes:

$R^1$, $R^2$, $R^4$ and Y being as defined in claim 3 and $R'^4$ representing an alkyl group exhibiting the same carbon number as the $R^4$ group and exhibiting an ethylenic unsaturation.

5. The process according to claim 3, which comprises a subsequent step of organometallic coupling between the trialkoxymetallated intermediate and a pi-conjugated system comprising $R^3$, $R^3$ being as defined in claim 3.

6. The process according to claim 1, which is carried out according to the following reaction scheme:

7. The process according to claim 1, which is carried out according to the following reaction scheme:

-continued

4

8. A process for the preparation of a chromophore being 5,5'-(1E,1'E)-2,2'-(2,5-bis(octyloxy)-1,4-phenylene)bis(ethane-2,1-diyl)bis(2-(4-(3-(triethoxysilyl)-propoxy)cyclohexyl)isoindoline-1,3-dione), which is carried out according to the following reaction scheme:

9. A sol-gel process for manufacturing a thin film comprising a step consisting of:

providing a chromophore of general formula:

-continued in which:
R$^1$ represents C$_1$-C$_4$ alkyl;
R$^2$ represents a sterically hindered group;
R$^3$ represents a pi-conjugated system;
Y represents O, S, NH or is absent;
R$^4$ represents a C$_3$-C$_{18}$ alkyl group;
M represents a metal from Group III including Group III-A and Group III-B or from Group IV including Group IV-A and Group IV-B of the Periodic Table;
n is an integer,
wherein the sterically hindered group is chosen from the group consisting of:

and
wherein R$^3$ is chosen from the group consisting of:

-continued with R representing H or a C$_1$-C$_{18}$, alkyl group, said alkyl group optionally being branched or substituted by a heteroatom chosen in the group consisting of O, S and N or a chromophore as prepared in any one of claim 1, 3 or 8 as a thin film precursor; and
forming the thin film.

10. A method for the stabilization of the J-type aggregation in a thin film comprising the steps consisting of:
providing a chromophore of general formula:

in which:
R$^1$ represents C$_1$-C$_4$alkyl;
R$^2$ represents a sterically hindered group;
R$^3$ represents a pi-conjugated system;
Y represents O, S, NH or is absent;
R$^4$ represents a C$_3$-C$_{18}$ alkyl group;

M represents a metal from Group III including Group III-A and Group III-B or from Group IV including Group IV-A and Group IV-B of the Periodic Table;
n is an integer,
wherein the sterically hindered group is chosen from the group consisting of:

and
wherein $R^3$ is chosen from the group consisting of:

with R representing H or a $C_1$-$C_{18}$, alkyl group, said alkyl group optionally being branched or substituted by a heteroatom chosen in the group consisting of O, S and N as a thin film precursor, and
forming the thin film.

11. The method according to claim 10, wherein the sterically hindered group is chosen from the group consisting of:

and the crosslinkable group is a silylated group.

12. The method according to claim 10, wherein the sterically hindered group is the cyclohexyl and the crosslinkable group $(M(OR^1)_3$ is trimethoxysilyl or triethoxysilyl.

13. The process according to claim 3, which is carried out according to the following reaction scheme:

14. The process according to claim 3, which is carried out according to the following reaction scheme:

15. The process according to either of claim 1 or 3 wherein M represents Si.

16. The sol gel process according to claim 9, wherein M represents Si.

17. The method according to any one of claims 10-12 wherein M represents Si.

18. The process according to either of claim 1 or 3, wherein the chromophore is 5,5'-(1E,1'E)-2,2'-2,5-bis(octyloxy)-1,4-phenylene)bis(ethene-2,1-diyl)bis(2-(4-(3-(triethoxysilyl)-propoxy)cyclohexyl)isoindoline-1,3-dione).

19. The sol gel process according to claim 9, wherein the chromophore is 5,5'-(1E,1'E)2,2'-(2,5-bis(octyloxy)-1,4-phenylene)bis(ethene-2,1-diyl)bis(2-(4-(3-(triethoxysilyl)-propoxy)cyclohexyl)isoindoline-1,3-dione).

20. The method according to any one of claims 10-12, wherein the chromophore is 5,5'-(1E,1'E)-2,2'-(2,5-bis(octyloxy)-1,4-phenylene)bis(ethene-2,1-diyl)bis(2-(4-(3-(triethoxysilyl)-propoxy)cyclohexyl)isoindoline-1,3-dione).

* * * * *